(12) United States Patent
Cizerle

(10) Patent No.: US 10,244,198 B2
(45) Date of Patent: Mar. 26, 2019

(54) MONITORED MOBILE PERSONAL SUBSTANCE TESTING SYSTEM

(71) Applicant: James Kirk Cizerle, Norfolk, VA (US)

(72) Inventor: James Kirk Cizerle, Norfolk, VA (US)

( * ) Notice: Subject to any disclaimer, the term of this patent is extended or adjusted under 35 U.S.C. 154(b) by 336 days.

(21) Appl. No.: 15/183,500

(22) Filed: Jun. 15, 2016

(65) Prior Publication Data
US 2017/0302880 A1 Oct. 19, 2017

Related U.S. Application Data

(60) Provisional application No. 62/322,199, filed on Apr. 13, 2016.

(51) Int. Cl.
| | |
|---|---|
| A61B 5/1171 | (2016.01) |
| A61B 10/00 | (2006.01) |
| A61B 5/08 | (2006.01) |
| H04N 5/77 | (2006.01) |
| A61B 5/00 | (2006.01) |
| H04W 4/60 | (2018.01) |
| G01N 1/00 | (2006.01) |
| G01N 1/02 | (2006.01) |

(52) U.S. Cl.
CPC ............ *H04N 5/772* (2013.01); *A61B 5/082* (2013.01); *A61B 5/1176* (2013.01); *A61B 5/4833* (2013.01); *A61B 10/0051* (2013.01); *H04N 5/77* (2013.01); *H04W 4/60* (2018.02); *A61B 5/4845* (2013.01); *A61B 2010/0009* (2013.01); *B01L 2200/185* (2013.01); *B01L 2300/021* (2013.01); *B01L 2300/024* (2013.01); *B01L 2300/042* (2013.01); *G01N 2001/005* (2013.01); *G01N 2001/027* (2013.01)

(58) Field of Classification Search
CPC ... A61B 10/0051; A61B 5/082; A61B 5/4845; A61B 5/4833; A61B 5/1176; A61B 5/103; A61B 5/002; A61B 5/0022; A61B 5/6898; A61B 2010/0009; G01N 33/94; G01N 33/98; G01N 2001/005; B01L 2200/185; H05N 5/772; H05N 5/77
See application file for complete search history.

(56) References Cited

U.S. PATENT DOCUMENTS

| | | | |
|---|---|---|---|
| 2010/0204600 A1* | 8/2010 | Crucilla | A61B 5/097 600/532 |
| 2011/0144454 A1* | 6/2011 | Koester | A61B 3/112 600/301 |

* cited by examiner

*Primary Examiner* — Christopher Adam Hixson
(74) *Attorney, Agent, or Firm* — Michael L. Greenberg, Esq.; Greenberg & Lieberman, LLC

(57) ABSTRACT

A system for testing an individual for illicit or other substances is described. The system operates in tandem with a mobile device (smartphone) application, which employs a camera of the mobile device to capture and record the self-administered specimen collection process for verification and rule compliance. The system guides the user through the process via on-screen prompts on the mobile device, and includes tracking of the collected specimen from the moment of collection until it is sealed in a tamper-proof container to be mailed for external testing at a lab. A breathalyzer may also be used with the system to test for the presence of alcohol in the user's body, the use of which is also monitored and recorded via the on-board camera of the mobile device for verification.

6 Claims, 3 Drawing Sheets

MONITORED MOBILE PERSONAL SUBSTANCE TESTING SYSTEM

This application is a non-provisional application of provisional patent application No. 62/322,199, filed on Apr. 13, 2016, and priority is claimed thereto.

FIELD OF THE PRESENT INVENTION

The present invention relates generally to methods of substance testing of an individual to produce testing data, and more specifically relates to a at-home substance testing system, the process of which is monitored for compliance and authenticity via a mobile device application.

BACKGROUND OF THE PRESENT INVENTION

Many companies deal with work that is time sensitive, safety-conscious, or that involve children. In these fields, as well as many others, individual drug and other substance tests are often required by a company prior to hiring an individual. These tests are often funded by the hiring company, which adds expenses to the hiring process. Usually the tests are conducted off-site, at an accredited and registered testing facility, where the individual can be monitored for compliance and guided through the test by an administrator. While effective, this process can add a good deal of time to the hiring process, resulting in lost time. The costs are often exasperated by costly paraprofessional services. If there were a cost-effective and verifiable method by which individuals can perform a monitored oral fluid specimen collection that is monitored by a camera, most substance testing could be achieved effectively via mail and/or via an at home testing device (such as for blood alcohol content).

Thus, there is a need for a system that facilitates an independent, yet monitored, substance testing system to be performed by the individual to be tested from within the comfort of his or her own home. Such a system preferably verifies the authenticity of the specimen sample to be tested by witnessing the sampling process via the onboard camera of a mobile device.

SUMMARY OF THE PRESENT INVENTION

The present invention is a substance testing system which is self-administered by the individual to be tested. The system employs a proprietary mobile device application for use on internet-enabled mobile devices, such as tablets and smartphones, which are equipped with an on-board camera. The system of the present invention has three primary components: the mobile device application, the specimen collection and mailing kit, and peripheral testing equipment, such as a breathalyzer.

BRIEF DESCRIPTION OF THE DRAWINGS

The present invention will be better understood with reference to the appended drawing sheets, wherein.

DETAILED DESCRIPTION OF THE PREFERRED EMBODIMENT

Figure 2:
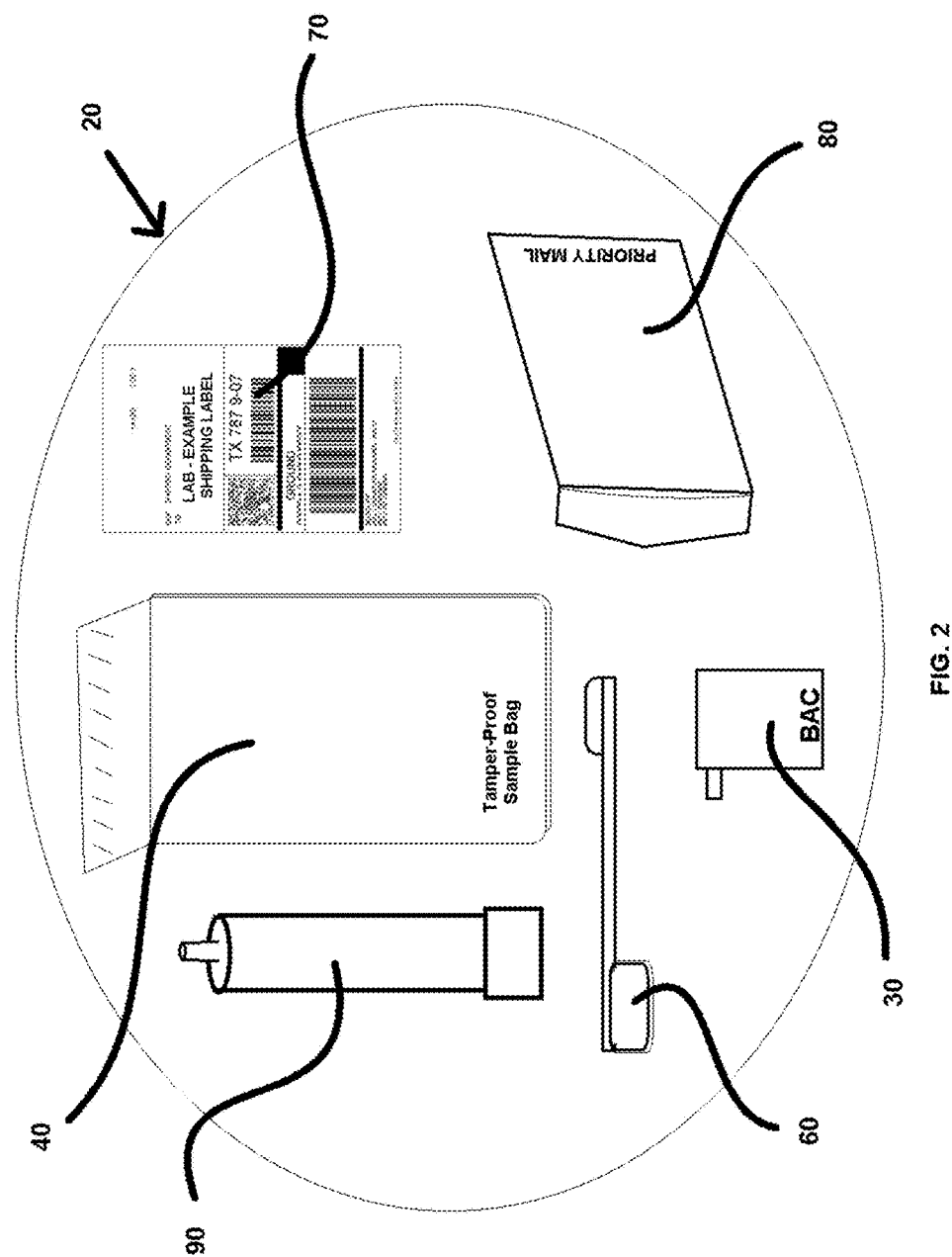
FIG. 2 exhibits a top view of the components contained within the specimen collection and mailing kit of the present invention.
Figure 3:
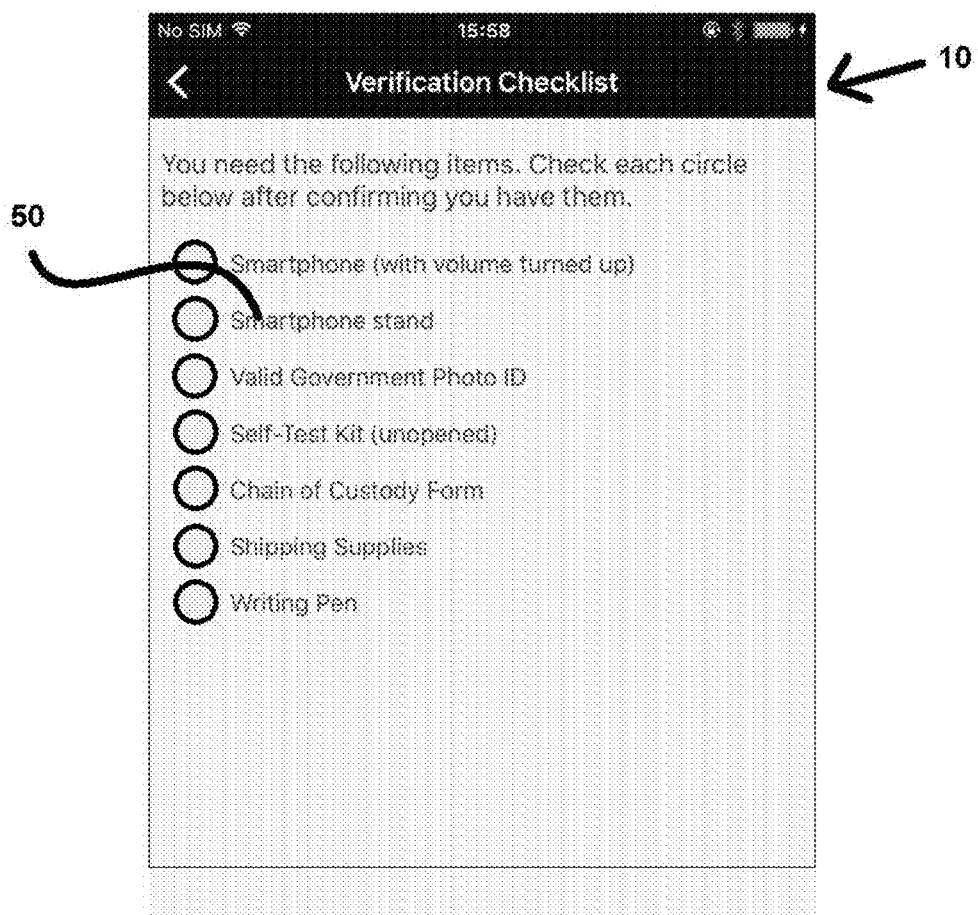
FIG. 3 displays a screenshot of the companion mobile device application showing the verification checklist.

Referring to the drawings and the characters of reference marked thereon, FIG. 2 displays the primary components of the present invention, which include: a mobile device application (10), a specimen collection and mailing kit (20), and a breathalyzer (30). All embodiments of the present invention need not include the breathalyzer (30), and may include a different peripheral instead of the breathalyzer (30). The specimen collection and mailing kit (20) preferably includes an oral fluid collection pad (60), a pre-addressed shipping label (70), a shipping envelope (80), an oral specimen collection vial (90), and a tamper-evident sample bag (40). To use the system of the present invention, the user (individual to be tested) acquires the specimen collection and mailing kit (20) from a retailer, e-retailer, or from the workplace in cases of pre-hire substance testing. The user is then instructed to download a mobile device application (10) which acts as a companion to the specimen collection and mailing kit (20), providing instructions for use of the system of the present invention, as well as a means to capture, record, and transmit authentication video of the specimen collection event. It should be understood that the specimen collection and mailing kit (20) is configured for the testing of a wide variety of panels, including any and all drugs/alcohol observable via the collected specimen medium. The system of the present invention provides a complete chain of custody of the collected sample specimen, and provides accurate, reliable results.

The mobile device application (10) of the present invention is configured to collect and store donor information, provide a tutorial to the donor (user) that meets or exceeds collector training requirements, provides step-by-step instructions, and enables the user to locate and access shipping providers to facilitate the mailing of the specimen via postal service pick-up from the home or workplace of the user. Throughout the process of specimen collection, the donor (user) is monitored and recorded via the on-board camera of the mobile device. The recording is provided to the lab for verification of correct and legitimate sample collection from the correct individual, helping to prevent fraud, false negatives, and false positives. The observed collection of the specimen via the system of the present invention does not require a third-party specimen collector, company representative, or witness. Additionally, the need for a specified collection site is eliminated. The process of the system of the present invention greatly reduces the opportunity for adulteration of the specimen, and eliminates 'collector error' issues.

Figure 1:
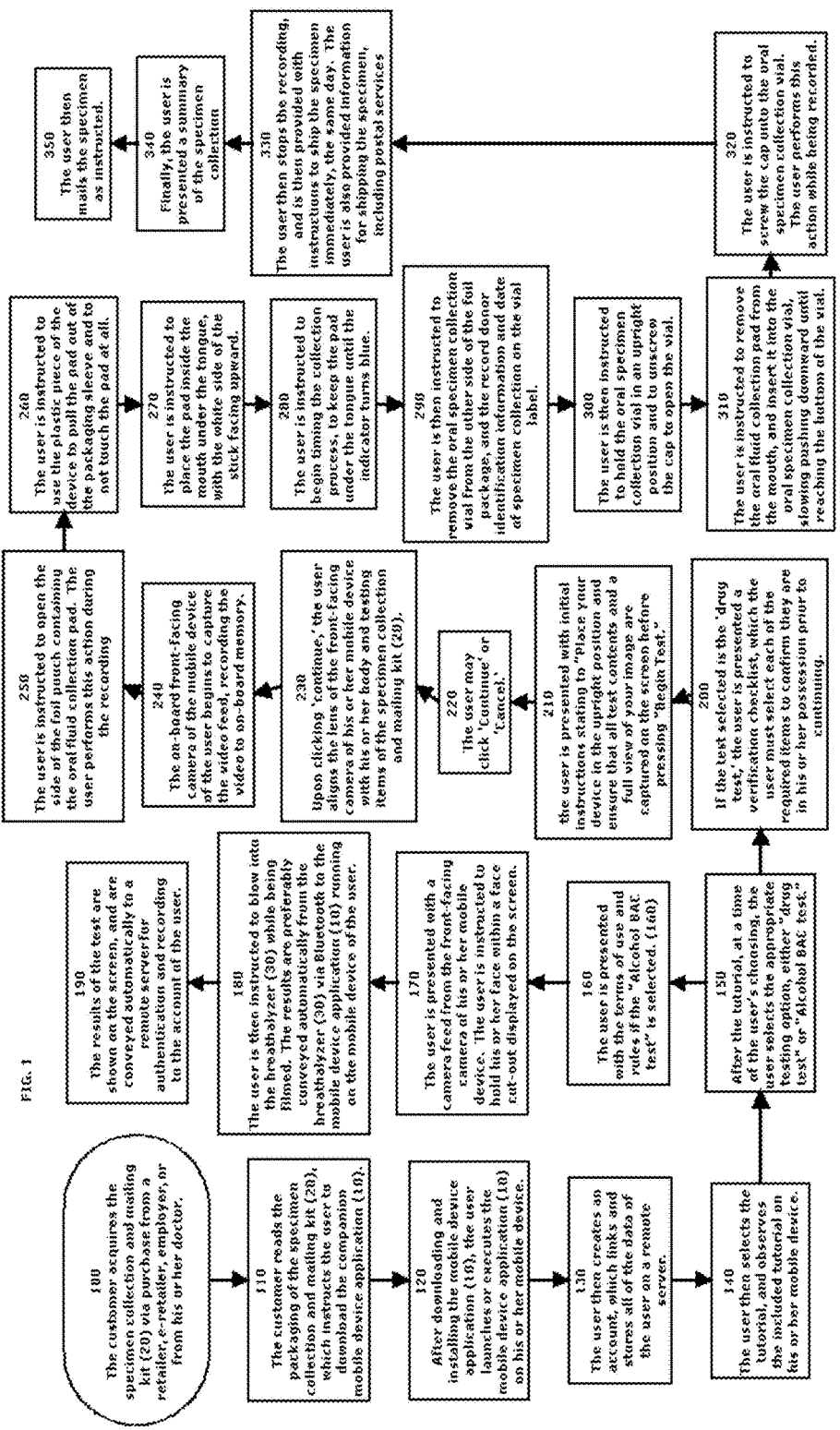
FIG. 1 exhibits a flow chart depicting the preferred process of use of the system of the present invention.

The process of use of the present invention, as depicted in FIG. 1, is preferably as follows:

1. The customer acquires the specimen collection and mailing kit (20) via purchase from a retailer, e-retailer, employer, or from his or her doctor. (100)
2. The customer reads the packaging of the specimen collection and mailing kit (20), which instructs the user to download the companion mobile device application (10). (110)
3. After downloading and installing the mobile device application (10), the user launches or executes the mobile device application (10) on his or her mobile device. (120)
4. The user then creates an account, which links and stores all of the data of the user on a remote server. The account creation includes the user listing his or her name, email, phone number and address, as well as creating a personal pin number for access. (130)
5. The user then selects the tutorial, and observes the included tutorial on his or her mobile device. (140)
6. After the tutorial, at a time of the user's choosing, the user selects the appropriate testing option, either "drug test" or "Alcohol BAC test." (150)
7. The user is presented with the terms of use and rules if the "Alcohol BAC test" is selected. (160) The rules include:
   1. "I will hold the device and look directly at my smartphone so that my head and face are within the 'guide' on the screen during the entire test process."
   2. "I will take a deep breath during the 'warm up' phase and blow steadily during the 'test' phase."
   3. "I will not attempt to obstruct the device or the mouthpiece in any way."
   4. "I will not wear anything on my face or head that would obstruct the camera and my photo during the test."
   5. "I will not place my hands or anything near the device or the mouthpiece."
   6. "I will not attempt to falsify the test or use any additional devices or assistance from other people to provide the device with a false reading."
8A. If performing the "Alcohol BAC test," the user is presented with a camera feed from the front-facing camera of his or her mobile device. The user is instructed to hold his or her face within a face cut-out displayed on the screen. (170)
9A. The user is then instructed to blow into the breathalyzer (30) while being filmed. The results are preferably conveyed automatically from the breathalyzer (30) via Bluetooth to the mobile device application (10) running on the mobile device of the user. (180)
10A. The results of the test are shown on the screen, and are conveyed automatically to a remote server for authentication and recording to the account of the user. (190)
8B. If the test selected is the 'drug test,' the user is presented a verification checklist (50), which the user must select each of the required items (materials) to confirm they are in his or her possession prior to continuing. (200) The checklist of materials includes the following items: a smartphone (with volume turned up), a smartphone stand, a valid government photo ID, the specimen collection and mailing kit (20), a chain of custody form, shipping supplies, and a writing pen.
9B. After completion of the verification checklist (50), the user is presented with initial instructions stating to "Place your device in the upright position and ensure that all test contents and a full view of your image are captured on the screen before pressing "Begin Test." (210)
10B. The user may click 'Continue' or 'Cancel.' (220)
11B. Upon clicking 'continue,' the user aligns the lens of the front-facing camera of his or her mobile device with his or her body and testing items of the specimen collection and mailing kit (20). (230)
12B. The on-board front-facing camera of the mobile device of the user begins to capture the video feed, recording the video to on-board (internal) memory. (240)
13B. The user is instructed to open the side of the foil pouch containing the oral fluid collection pad. The user performs this action during the recording. (250)
14B. The user is instructed to use the plastic piece of the device to pull the pad out of the packaging sleeve and to not touch the pad at all. The user then performs this step while being recorded. (260)
15B. The user is instructed to place the pad inside the mouth under the tongue, with the white side of the stick facing upward. The user is further instructed to avoid biting down on the plastic piece. The user performs this action while in the frame of the camera. (270)
16B. The user is instructed to begin timing the collection process, to keep the pad under the tongue until the indicator turns blue. The user performs this action while recorded. (280) The mobile device application (10) notes that the average collection times are three to four minutes. Should the collection time reach 15 minutes, stop the collection and proceed to the next step.
17B. The user is then instructed to remove the oral specimen collection vial from the other side of the foil package (of the specimen collection and mailing kit (20)), and the record donor identification information and date of specimen collection on the vial label in the space above the lot number, while being recorded. (290)
18B. The user is then instructed to hold the oral specimen collection vial in an upright position and to unscrew the cap to open the vial. The user is instructed to not spill or otherwise remove the fluid from the vial. The user then performs this action while being recorded. (300)
19B. After the specimen collection is complete, the user is instructed to remove the oral fluid collection pad from the mouth, and insert it into the oral specimen collection vial, slowly pushing downward until reaching the bottom of the vial. The user performs this step while being recorded on camera. (310) It is envisioned that the pad will be submerged in preservative solution.
20B. The user is instructed to screw the cap onto the oral specimen collection vial. The user performs this action while being recorded. (320)
21B. The user then stops the recording, and is then provided with instructions to ship the specimen immediately, the same day. The user is also provided information for shipping the specimen, including postal services that can facilitate the shipment. (330)
22B. Finally, the user is presented a summary of the specimen collection, including a confirmation number, date of collection, the collection start time, the collection end time, the collection elapsed time, and verification that the transmission of the summary to the remote server was successful. (340)
23B. The user then mails the specimen as instructed. (350)

It should be understood that, in some embodiments of the present invention, instructions provided by the companion application as listed in the steps above may be detailed solely in the tutorial portion in a step-by-step fashion. Similarly, the 'at-home' use of the present invention is not a limiting term, and as such, it is envisioned that the present invention may be used anywhere, including offices, outdoors, etc. Additionally, use of the present invention is not limited to use for a condition of hiring, and is envisioned for a wide range of testing uses beyond the hiring of employees.

Additionally, the mobile device application (10) may be equipped with facial recognition capabilities as a means to verify the identity of the user as he or she self-administers the test. In such an embodiment, the face of the user is captured via the front-facing camera of the mobile device, and the capture is compared to previous captures of the face of the user via the software of the mobile device application (10) to further verify the identity of the user, helping to ensure that a different individual is not taking the test.

Other alternate embodiments of the present invention include instant tests, which are configured to communicate the results of the instant test to the mobile device application (10) without delay, and potentially without the need to send the specimen collection vial (90) in for evaluation/testing. Additionally, some embodiments of the specimen collection and mailing kit (20) may present the user/individual with a test that can provide instant results to the user as well as to the mobile device application (10), which may then be relayed to the remote server and attributed to the account of the user.

Another alternate embodiment of the present invention includes the use of further identity verification of the user via the remote server. In such embodiments, the remote server preferably employs facial recognition to confirm that the user ID of the user matches the image of the user in the recorded video, which is transmitted to the remote server for storage and review. This confirmation of identity may employ base photos or videos of the user with which a computer may compare the live video feed and/or recorded video to the base photos or videos to facilitate a confirmation of the identity of the user.

Another alternate embodiment provides the use with more personalized instructions of use. For example, the mobile device application (10) may facilitate a one way or two way audio/video connection between the user and management, i.e. the testing company or similarly related company. In such embodiments, the one-way or two-way audio/video communication between the user and staff can facilitate correct use of the system of the present invention, as well as provide a live, alternative means of witnessing the user perform the self-administered test. In such embodiments, the user can opt to be personally guided by a live person through the self-testing process facilitated by the system of the present invention.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. A method for testing for substances within an individual, by the individual, via a sample specimen comprising:
    the individual acquiring a specimen collection and mailing kit;
    instructions of the specimen collection and mailing kit instructing the individual to download a companion application to a mobile device;
    the individual downloading the companion application to the mobile device;
    the individual launching the companion application on the mobile device;
    the individual creating an account on a screen of the mobile device;
    wherein the account is hosted on a remote server;
    the companion application displaying a tutorial to the individual on the screen of the mobile device;
    the tutorial including detailed instructions of the method;
    the companion application presenting the individual with terms of use on the screen of the mobile device;
    the individual confirming compliance of the terms of use;
    the companion application providing the individual testing options;
    wherein the testing options include a substance test and an alcohol BAC test;
    the individual selecting the substance test option on the screen of the mobile device;
    the companion application displaying a verification checklist including a list of required materials;
    the individual confirming possession of the required materials;
    the companion application instructing the individual to orient the mobile device in the portrait orientation;
    the companion application activating a front-facing camera of the mobile device;
    the companion application displaying a live video feed from the front-facing camera of the mobile device to the individual;
    the companion application instructing the individual to place the required materials in view of the front-facing camera such that it is shown on the live video feed;
    the companion application instructing the individual to position a face of the individual within the frame of the front-facing camera;
    the companion application recording the live video feed to internal memory of the mobile device;
    the companion application instructing the individual to remove an oral fluid collection pad from the specimen collection and mailing kit via a plastic handle;
    the companion application instructing the individual to not touch the oral fluid collection pad;
    the individual removing the oral fluid collection pad from the specimen collection and mailing kit via the plastic handle while being recorded;
    the companion application instructing the individual to place the oral fluid collection pad under a tongue of the individual until a portion of the oral fluid collection pad turns blue in color;
    the individual placing the oral fluid collection pad under the tongue of the individual while being recorded;
    the individual beginning a timer to capture the duration of time in which the oral fluid collection pad is disposed under the tongue of the individual;
    the companion application instructing the individual to remove an oral specimen collection vial while being recorded;
    the individual writing personal information and date of collection on the oral specimen collection vial;
    the individual opening a cap the oral specimen collection vial while being recorded;
    the individual removing the oral fluid collection pad from the mouth while being recorded;
    the individual placing the oral fluid collection pad into the oral specimen collection vial while being recorded;

the individual sealing the cap of the oral specimen collection vial while being recorded;

the individual stopping the recording from the camera via the screen of the mobile device;

the companion application providing shipping instructions instructing the individual to ship the oral specimen collection vial within one day;

the companion application displaying a summary of the specimen collection; and the individual shipping the oral specimen collection vial.

2. The method of claim 1, further comprising:

the individual selecting the alcohol BAC option;

the companion application displaying terms of use and rules pertaining to the alcohol BAC option;

the companion application activating the front-facing camera of the mobile device, producing a live-video feed on the screen of the mobile device;

the companion application instructing the individual to position the face of the individual within a face cut-out displayed over the live-video feed;

the individual placing his/her face within the face cut-out;

the companion application instructing the user to blow into a breathalyzer while remaining within the face cut-out, commencing a breathalyzer test;

conveying the results of the breathalyzer test to the companion application via the camera;

the companion application stopping the camera recording;

the companion application conveying the results of the breathalyzer test to the remote server for authentication;

the companion application conveying the recording from internal memory to the remote server; and the remote server mapping the recording and results of the breathalyzer test to the account of the individual.

3. The method of claim 2, wherein the terms of use and rules include the following statements:

"I will hold the device and look directly at my smartphone so that my head and face are within the 'guide' on the screen during the entire test process", "I will take a deep breath during the 'warm up' phase and blow steadily during the 'test' phase", "I will not attempt to obstruct the device or the mouthpiece in any way", "I will not wear anything on my face or head that would obstruct the camera and my photo during the test", "I will not place my hands or anything near the device or the mouthpiece", and "I will not attempt to falsify the test or use any additional devices or assistance from other people to provide the device with a false reading".

4. The method of claim 1, wherein said the individual creating an account includes the user listing his or her name, email, phone number, address, and an access pin.

5. The method of claim 1, wherein the list of required materials includes a mobile device, a mobile device stand, a valid government photo ID, the specimen collection and mailing kit, a chain of custody form, shipping supplies, and a pen.

6. The method of claim 1, wherein said oral fluid collection pad is stored within a foil pouch prior to use; and wherein said foil pouch is sterile.

* * * * *